(12) United States Patent
Kennedy et al.

(10) Patent No.: US 6,585,114 B2
(45) Date of Patent: Jul. 1, 2003

(54) LID FOR MEDICAL WASTE CONTAINER

(75) Inventors: Daniel Kennedy, Brampton (CA); Istvan Vaskuthy, Saint-Hyacinthe (CA)

(73) Assignees: Medical Waste Management Inc., Brampton (CA); VIF Mould and Plastic Industries Ltd., Saint-Hyacinthe (CA)

( * ) Notice: Subject to any disclaimer, the term of this patent is extended or adjusted under 35 U.S.C. 154(b) by 0 days.

(21) Appl. No.: 09/953,214

(22) Filed: Sep. 17, 2001

(65) Prior Publication Data

US 2003/0052027 A1 Mar. 20, 2003

(51) Int. Cl.$^7$ ................................. B65D 83/10

(52) U.S. Cl. ................. 206/366; 220/831; 220/908

(58) Field of Search .................... 206/365, 366, 206/370; 220/908, 825, 827, 831, 832

(56) References Cited

U.S. PATENT DOCUMENTS 5,415,315 A * 5/1995 Ramirez ................. 220/345.2
6,253,916 B1 * 7/2001 Bickel ........................ 206/366

* cited by examiner

*Primary Examiner*—Jacob K. Ackun
(74) *Attorney, Agent, or Firm*—Bereskin & Parr (57) ABSTRACT

A lid for a medical waste container which receives sharps waste such as hypodermic needles. The lid has a closure hinged to the lid by a flexible strap and movable between first and second recesses in the lid. The first recess is closed and simply receives and retains the closure when the lid is open for depositing waste. The second recess has an opening through which waste can be deposited into the container. A temporary locking mechanism retains the closure in the second recess by a snap fit but allows the closure to be lifted from the second recess to open the container. A permanent locking mechanism, when actuated, locks the closure in the second recess permanently so that the container is sealed for autoclaving and cannot be reopened.

13 Claims, 12 Drawing Sheets

DETAIL A

DETAIL A

DETAIL A

DETAIL A

LID FOR MEDICAL WASTE CONTAINER

FIELD OF THE INVENTION

This invention relates to a lid for a container which receives medical waste. The container is particularly intended to receive the barrels and needles of syringes.

BACKGROUND OF THE INVENTION

After medical syringes have been used, e.g. to take fluid samples from patients, or to inject medication into patients, the syringes must be disposed of. In some cases the syringe is disposed of as a complete unit, while in other cases the needle may be unscrewed from the barrel of the syringe, and the two components may be disposed of separately (although in some cases, they are still disposed of in the same container). Because of the presence of the sharp needles, this type of waste is commonly referred to in the medical profession as "sharps" waste.

Sharps waste can be hazardous to persons who may come in contact with such waste, since the needles may be and frequently are contaminated with dangerous biological materials. Therefore sharps waste must be disposed of, usually by a physician or a nurse, in a safe container where it is unlikely to cause injury while it is awaiting removal from the physician's office for permanent disposal.

BRIEF SUMMARY OF THE INVENTION

It is therefore an object of the present invention to provide a lid for a container for medical waste, which lid is convenient and relatively safe to use.

In one aspect the invention provides a lid for a medical waste container, said lid comprising:
 (a) a closure hinged to said lid and movable between a first closed position and a second open position;
 (b) first and second recesses in said lid for receiving said closure when said closure is in its first and second positions respectively;
 (c) said first recess being closed and serving only to house said closure when said lid is to be open for depositing said waste;
 (d) said second recess having an opening therein to allow waste to be deposited therethrough into said container;
 (e) said closure and said second recess including at least one cooperative locking mechanism for retaining said closure in said second recess, to close said opening in said second recess.

Further objects and advantages of the invention will appear from the following description, taken together with the accompanying drawings.

DETAILED DESCRIPTION OF THE PREFERRED EMBODIMENT

Figures 1, 1A:
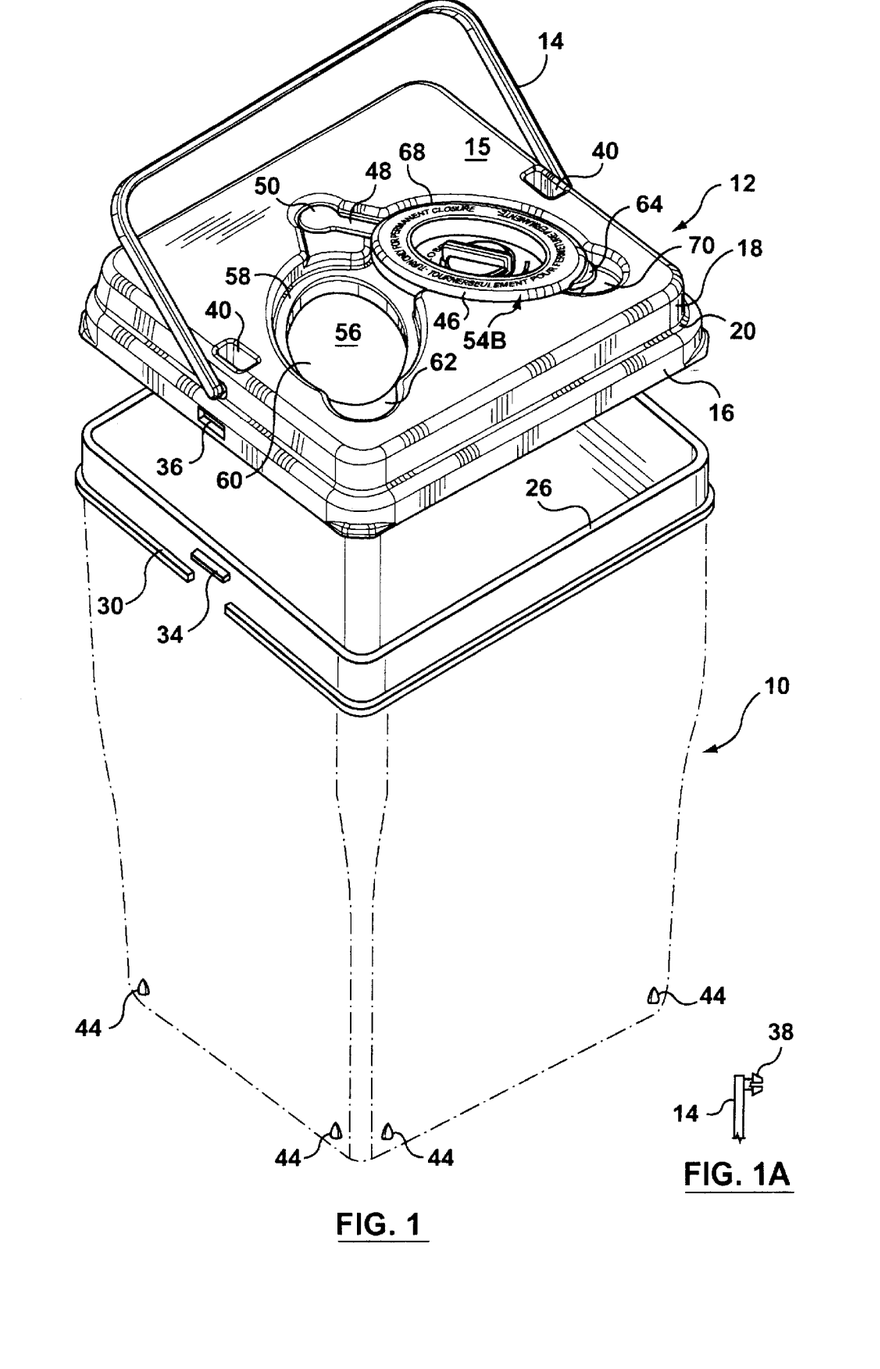
FIG. 1 is a perspective view of a lid according to the invention, with the lid spaced above a container.
FIG. 1A is a partial view of a snap fit pivot for the handle of the FIG. 1 lid.
Figure 4:
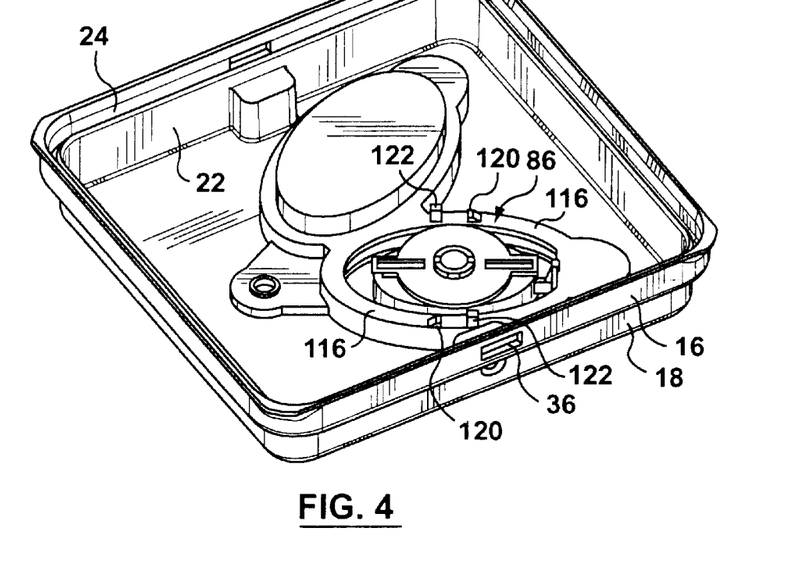
FIG. 4 is a bottom isometric view of the FIG. 1 lid, with the closure in temporary closed position.
Figure 5:
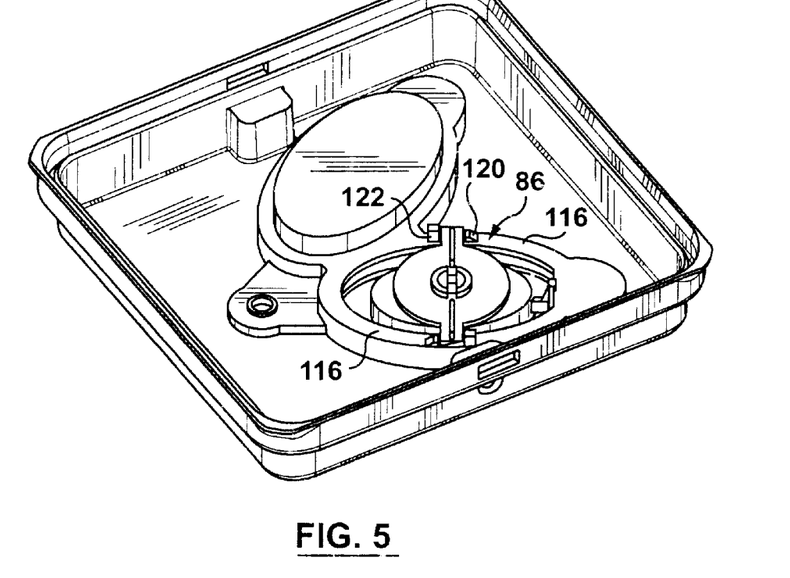
FIG. 5 is a bottom isometric view similar to that of FIG. 4 with the closure in permanent closed position.
Figure 6:
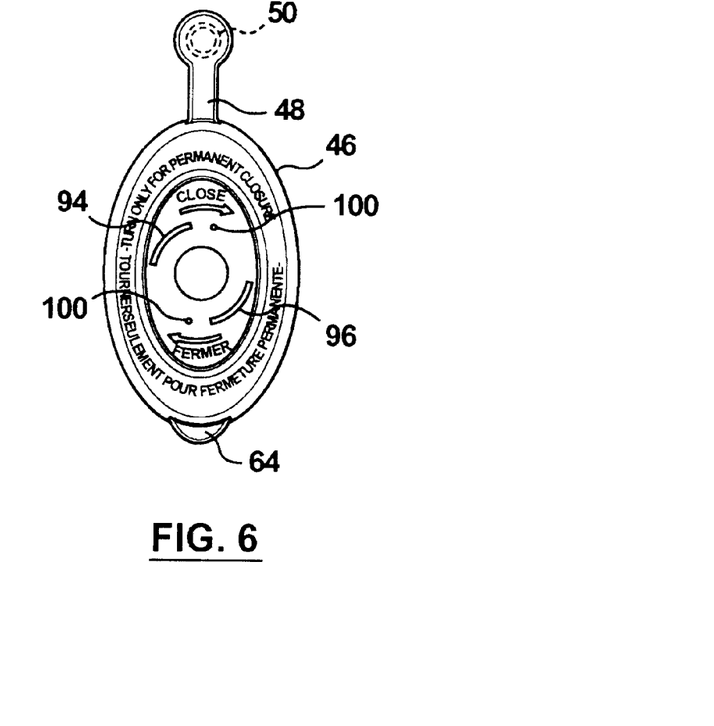
FIG. 6 is a top view of the closure for the FIG. 1 lid, with the permanent locking mechanism omitted.
Figures 7, 8:
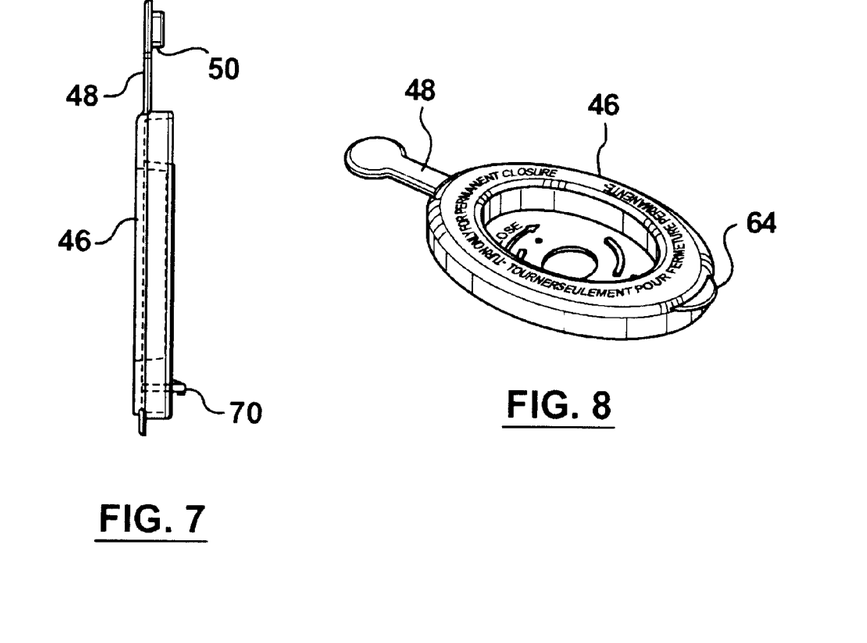
FIG. 7 is a side view of the FIG. 6 closure.
FIG. 8 is an isometric view of the FIG. 6 closure.
Figure 9A:
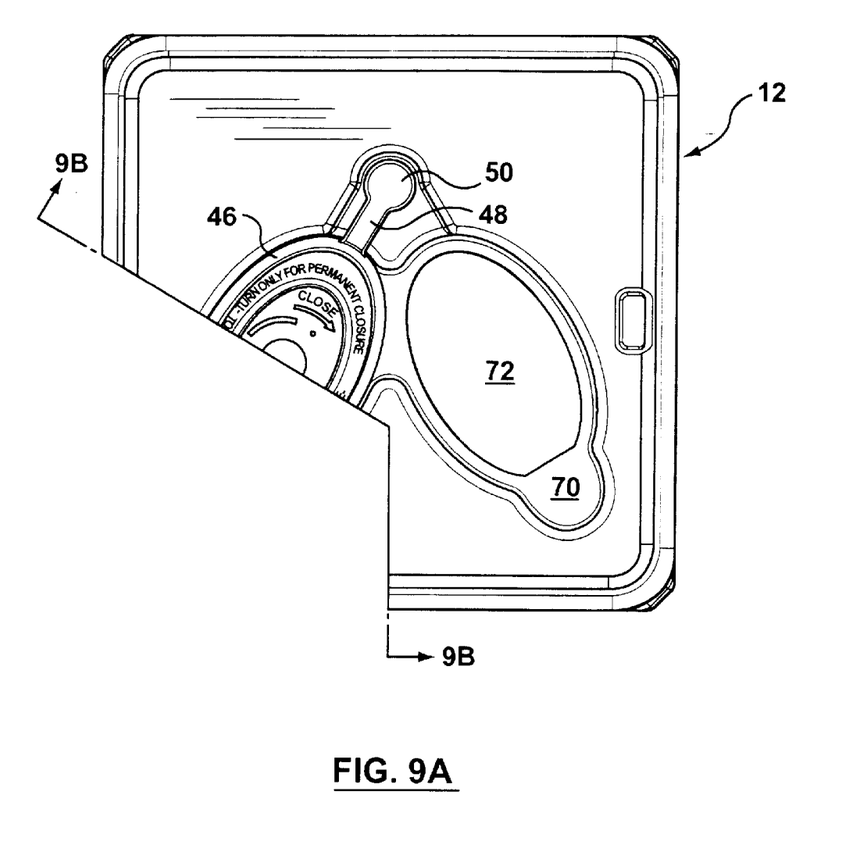
FIG. 9A is a top partial view of the FIG. 1 lid, with the closure in "open" position and showing section lines for FIG. 9B.
Figure 9B:
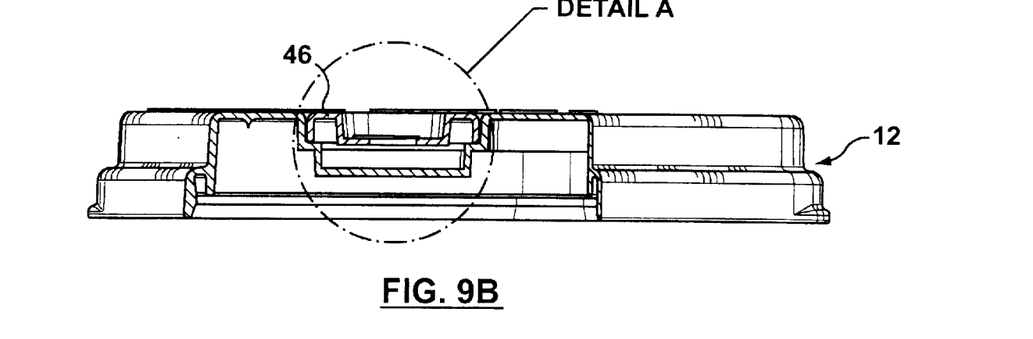
FIG. 9B is a section taken along lines 9B—9B of FIG. 9A.
Figure 9C:
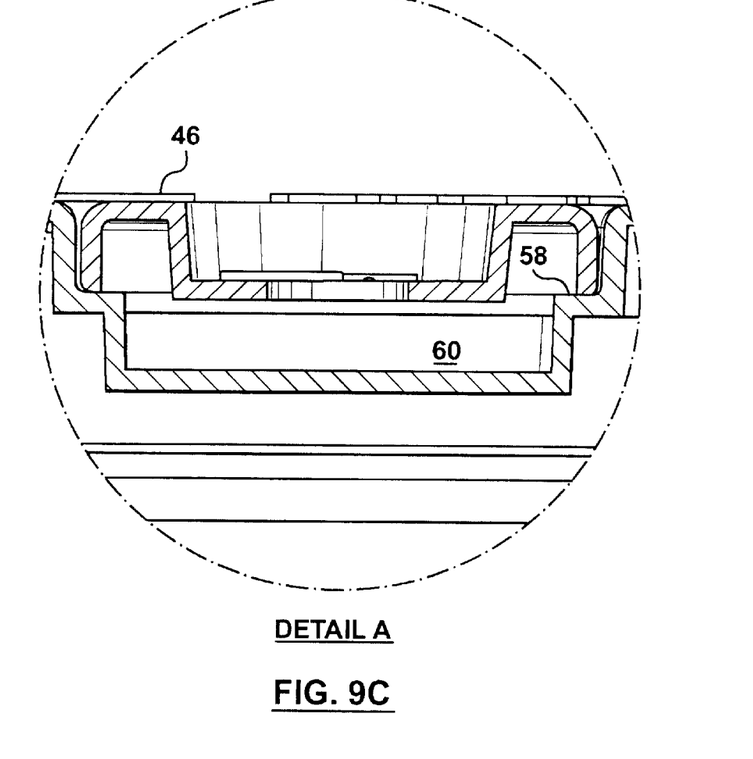
FIG. 9C is a n enlarged view of detail A of FIG. 9B.
Figure 15:
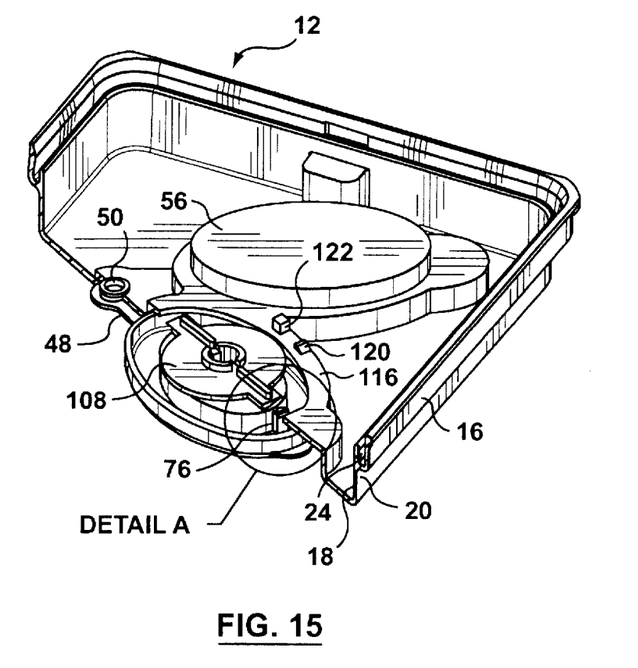
FIG. 15 is a bottom sectional view of the FIG. 1 lid showing the temporary locking mechanism and showing the permanent locking mechanism in its open condition.
Figure 16:
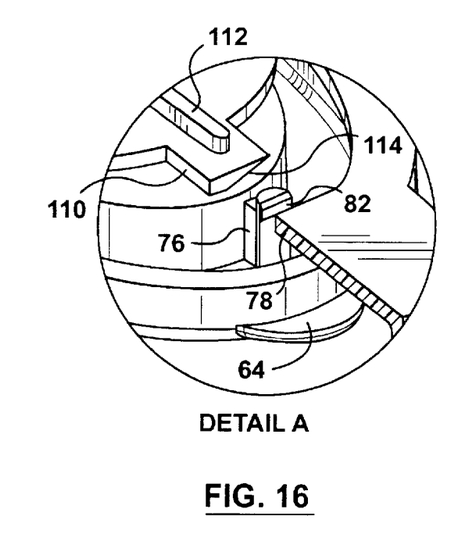
FIG. 16 is an enlarged view of detail A of FIG. 15 and showing the temporary locking mechanism.

Reference is first made to FIG. 1, which shows a medical waste container 10 bearing a lid 12 having a handle 14. As shown, the lid 12 is of generally square configuration (although it can, of course, be round, elliptical or of other outline), with an upper surface 15, a lower encircling perimeter wall 16 and an upper encircling perimeter wall 18 inset slightly from the lower wall 16 and joined to the lower wall by a ledge 20. As seen from the inside of the lid 12 (FIGS. 4, 15), an extension 22 of the upper wall 18 extends downwardly inside and parallel to the lower wall 16, forming a channel 24 which receives the upper edge 26 of the container 10.

An outwardly extending ridge 30 encircles the outer wall 32 of the container 10 and serves as a stop to position the lid 12 accurately on the container.

Short projections 34 near the top of the container (above ridge 30) protrude through openings 36 in the lower lid wall 16 to provide a snap fit when the lid is placed on the container, ensuring that the lid 12 will remain in position on the container.

The handle 14 is hinged to the upper wall 18 by snap-fit stub pivot shafts 38 (FIG. 1A) which protrude into closed wells 40 in the lid upper surface 15. The handle 14 permits a user to lift the container, with reduced risk of encountering a needle which may have thrust through the wall of the container body. However the container body and lid are both preferably formed from a strong material such as polypropylene, which is highly resistant to being penetrated by a needle tip.

Figure 2:
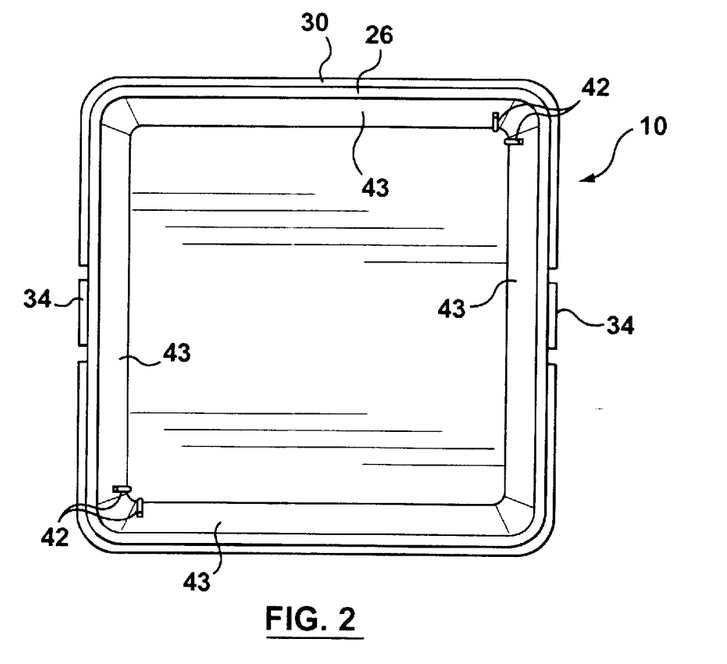
FIG. 2 is a top view of the FIG. 1 container.

The container 10 tapers slightly inwardly in a downward direction, so that a number of containers 10 can be nested for storage prior to use. However as an added precaution to prevent weakening of the containers when they are nested, each container 10 contains two pairs of internal ridges 42 (FIG. 2), one pair at each of two opposed corners, extending from the container bottom partway up the inner wall 43 of the container as shown. Each container also has four slightly protruding external pairs of legs 44 at its bottom outer surface, one pair at each corner. When the containers 10 are nested, the legs 44 encounter and are stopped by the inner ridges 42, preventing an inner container from being forced too far into an outer container and thereby weakening the outer container. Instead, during nesting, the containers stack with the bottom of one container spaced from the bottom of the container in which it is nested.

The lid 12 includes a closure 46 having an integral flexible strap 48 protruding from one end of the closure. (See also FIGS. 6–9) The strap 48 is pivotally mounted to the lid upper surface 15 at pivot mounting 50 (which is a conventional plastic hinge) so that the closure 46 can move between an open position 54A (FIG. 3) and a closed position 54B (FIG. 1). In the closure's open position 54A, the closure 46 is housed in a recess 56 in the lid upper surface 15. The recess 56 includes a recessed outer portion 58 (FIG. 1) shaped to accommodate the closure 46, and a further recessed central portion 60 which receives and accommodates the closure locking mechanism (to be described), so that the upper surface of the closure 46 is approximately flush with the lid upper surface 15. An extension 62 of the recess outer portion 58 receives a finger tab 64 extending from the closure 46 at the opposite end from the strap 48.

Figure 3:
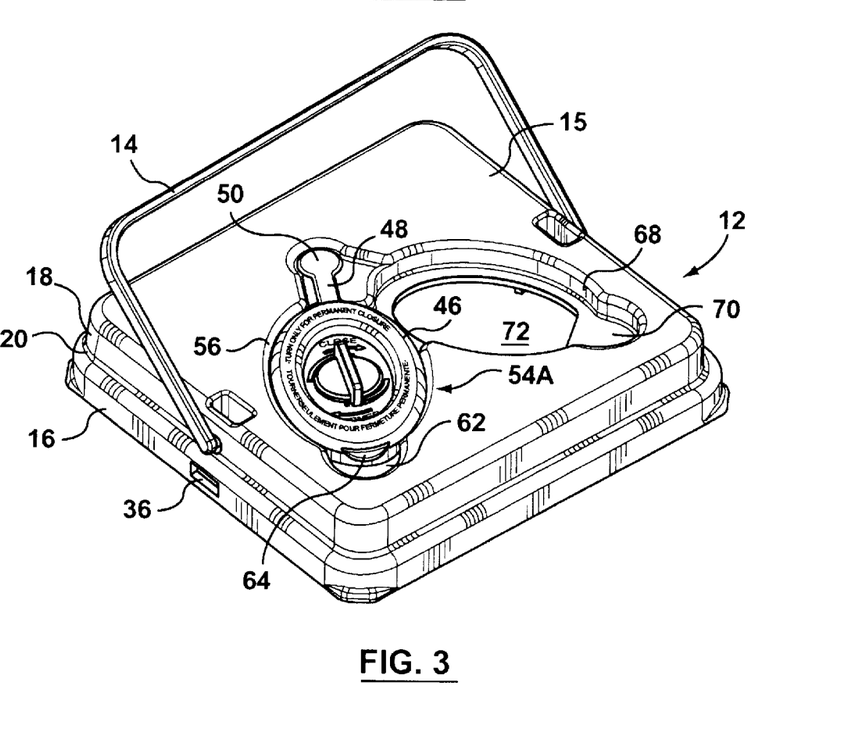
FIG. 3 is a top isometric view of the FIG. 1: lid, with the closure in "open" position.

The recess 56 is shaped and dimensioned to accommodate the closure 46 relatively snugly, preferably with enough friction to prevent the closure from "flopping" loosely, but with sufficient tolerance to allow a small lifting force applied by a finger on the tab 64 to lift the closure 46 from the recess 56, (bending strap 48 upwardly at this time) and then swinging the closure to its closed position 54B. The recess extension 62 is sufficiently larger than the finger tab 64 on the closure to allow a finger to be inserted under the extension tab 62 to lift the closure for a movement to its closed position 54B. The recess 56 is "closed", i.e. it has no openings from its upper to its lower surface.

The lid 12 also contains a second upper recess 68 (FIG. 3), located at the closed position 54B. Recess 68 has the same shape as the first upper recess 56, including an extension recess 70 for the finger tab 64. However the second recess 68, instead of containing a central recess like recess 56, instead contains an opening 72 through which syringe needles and barrels and complete syringes may be deposited into the waste container 10. The opening 72 is of convenient size for this purpose and may for example be between one and two inches wide at its widest portion, and between two and three inches long. In a preferred embodiment the opening 72 was approximately 1.40 inches wide at its widest dimension and was approximately 2.27 inches long at its longest dimension.

After a syringe or a needle or a syringe barrel has been deposited in the container 10, but when the container 10 is not yet full, it is usually desired to close the container temporarily (using the closure 46), until the next deposit. After the container is full, it is desired to lock the closure 46 permanently in closed position, so that it cannot readily be opened from outside the container.

For this purpose the closure 46 includes two locking mechanisms, one of which holds the closure temporarily in closed position 54B, and the other of which can hold the closure permanently in closed position 54B.

Figure 10A:
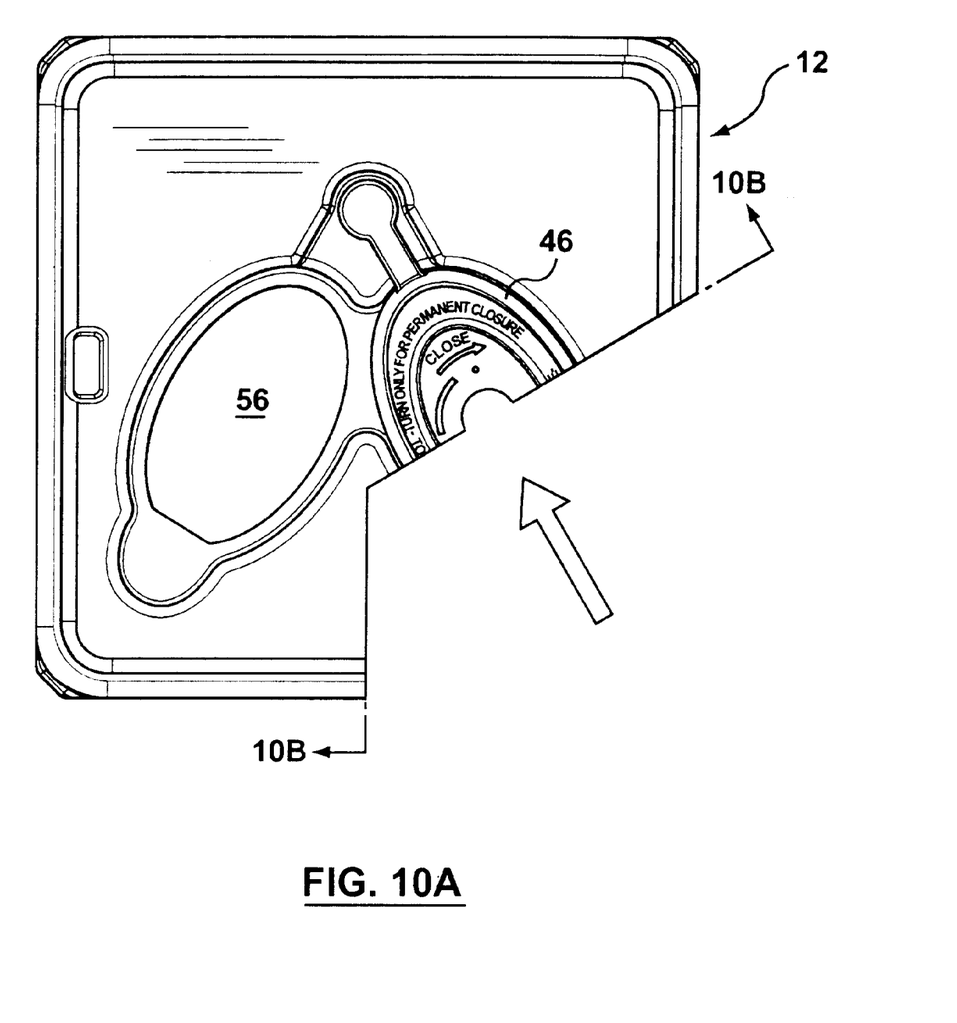
FIG. 10A is a top view of the FIG. 1 lid and showing section lines for FIG. 10B.
Figure 10B:
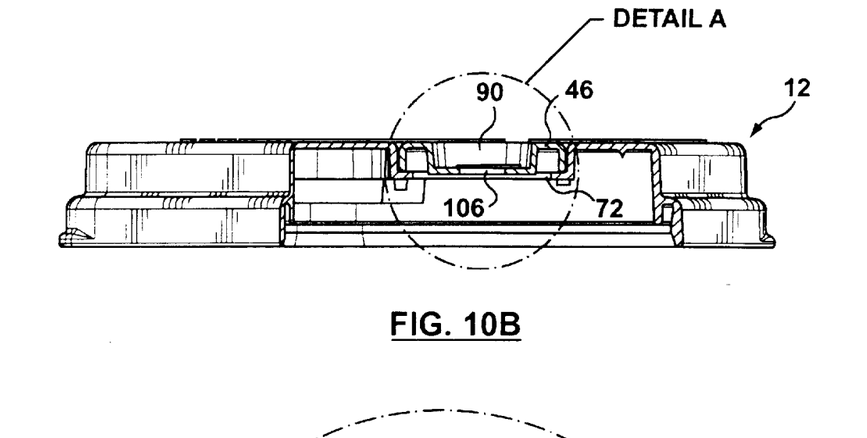
FIG. 10B is a section taken along lines 10B—10B of FIG. 10A.
Figure 10C:
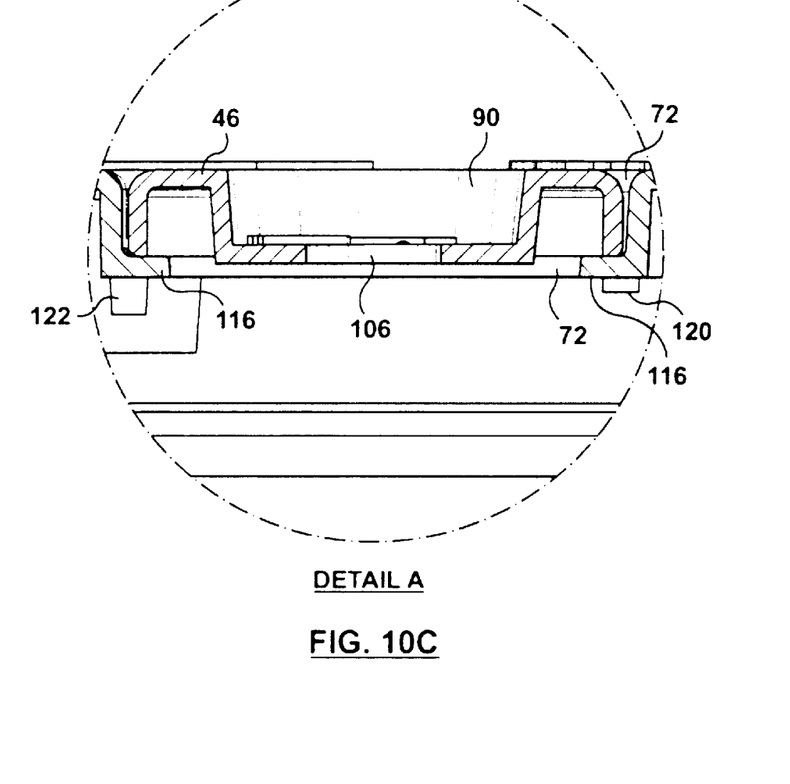
FIG. 10C is an enlarged view of detail A of FIG. 10B.
Figure 11A:
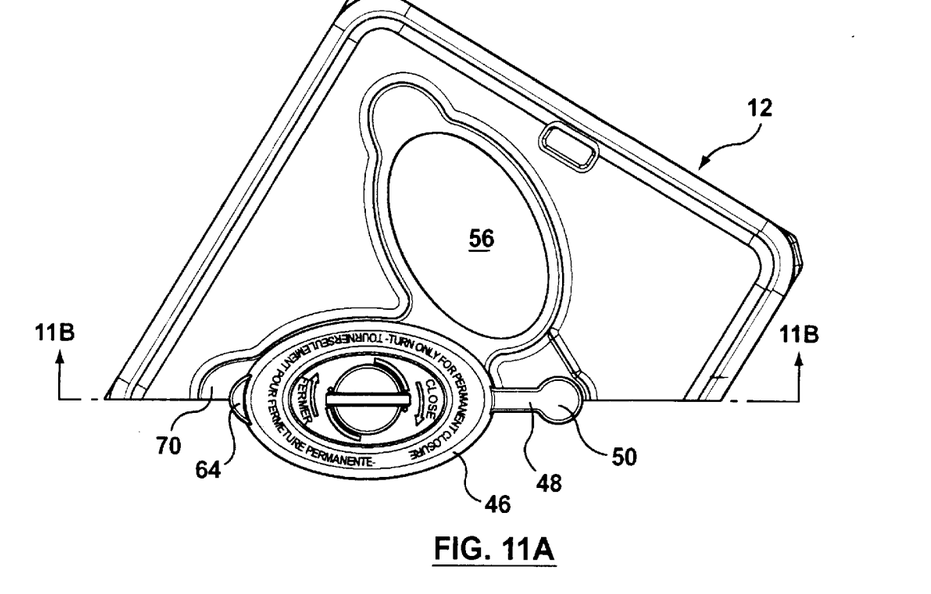
FIG. 11A is a top view of the FIG. 1 lid with the closure in "closed" position and showing section lines for FIG. 11B.
Figure 11B:
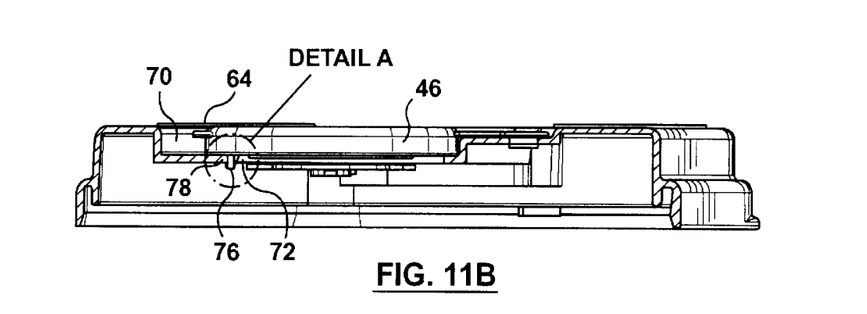
FIG. 11B is a section taken along lines 11B—11B of FIG. 11A.
Figure 11C:
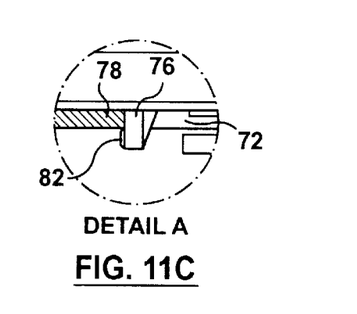
FIG. 11C is an enlarged view of detail A of FIG. 11 B.
Figure 12A:
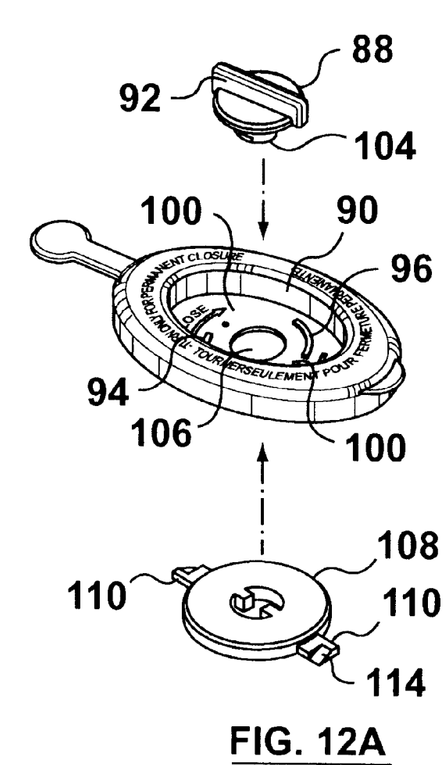
FIG. 12A is an exploded isometric view of the closure for the FIG. 1 lid and showing in particular a portion of the permanent locking mechanism.
Figure 12B:
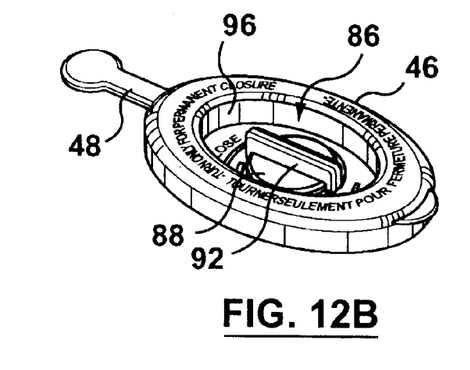
FIG. 12B is a top isometric view of the FIG. 12A closure.
Figure 12C:
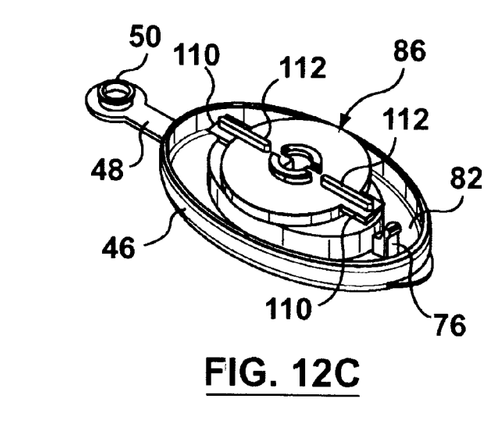
FIG. 12C is a bottom isometric view of the FIG. 12A closure.
Figure 13A:
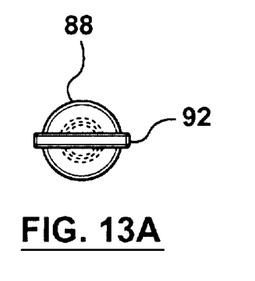
FIG. 13A is a top view of a button forming part of the permanent locking mechanism for the FIG. 12A closure.
Figure 13B:
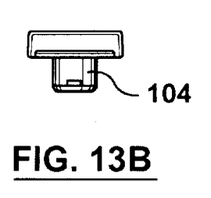
FIG. 13B is a side view of the FIG. 13A button.
Figure 13C:
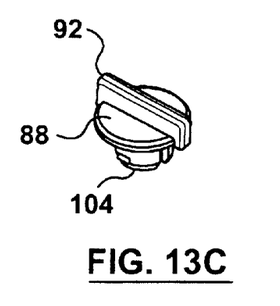
FIG. 13C is a top isometric view of the FIG. 13A button.
Figure 13D:
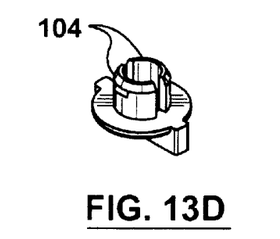
FIG. 13D is a bottom isometric view of the FIG. 13A button.
Figure 14A:
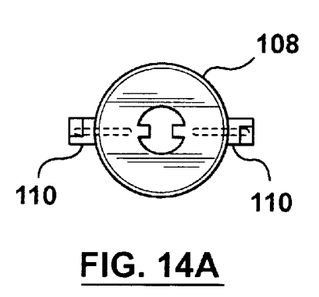
FIG. 14A is a top view of a washer for the permanent locking mechanism for the FIG. 12A closure.
Figure 14B:
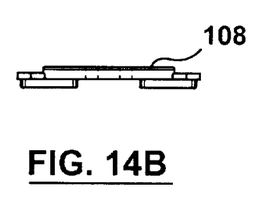
FIG. 14B is a side view of the FIG. 14A washer.
Figure 14C:
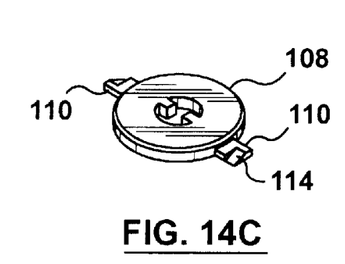
FIG. 14C is a top isometric view of the FIG. 14A washer.
Figure 14D:
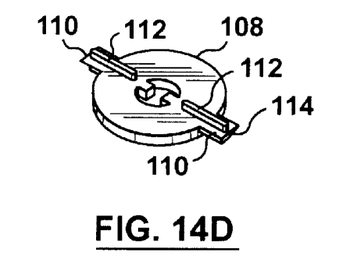
FIG. 14D is a bottom isometric view of the FIG. 14A washer.

The temporary locking mechanism (see particularly FIGS. 11A, 11B, 11C, 16) comprises a post 76 which extends downwardly from the lower surface of the closure 46, near the finger tab 64, and in a position in which it interferes slightly with the edge 78 of the opening 72. The lower surface 80 of the post includes a short forwardly projecting tab 82 as best shown in FIG. 10C, so that as the post lower surface 80 (which is formed of polypropylene) encounters the edge 78, the post is cammed inwardly allowing the tab 82 at the bottom of the post 76 to snap under the edge of the opening 72, thus holding the closure 46 in closed position by this snap-fit. To open the closure 46, upward pressure is exerted on the finger tab 64, thus forcing the thin post 76 to move inwardly and allowing the closure 46 to be opened for a new deposit.

For more secure temporary locking, and also for permanent locking, of the closure 46 in closed position 54B, a locking mechanism 86 is provided (FIGS. 4, 5, 12–16). The locking mechanism 86 includes a circular flat button 88 mounted in a recess 90 in closure 46.and having a diametrical ridge 92 extending upwardly from the upper surface of the button 88. The ridge 92 can be grasped to rotate the button 88. As shown, the ridge 92 extends diametrically slightly beyond the circumference of the button on each side of the button and encounters stop ridges 94, 96 (see also FIG. 6) formed on the upper surface of the closure recess 90, so that the button 88 can be rotated only from the position shown in FIG. 1 or 3 (parallel to the longitudinal axis 98 of the closure 46) clockwise to a position 90 degrees from the position shown in FIG. 1 or 3 (at which time the ridge 92 again encounters the stop ridges 94, 96 and is prevented from further rotation). Small raised projections 100. (FIG. 6) (which look like dots) extend upwardly from the bottom upper surface of recess 90 and offer modest resistance to rotation of ridge 92 over them, to prevent button 88 from accidentally being rotated from its unlocked position towards its locked position.

The button 88 is secured, by a protruding snap fit pair of integral members 104 (FIG. 13) which extend through opening 106 in the closure recess 90, and through a washer 108. Washer 108 is circular and generally of flat disc shape but contains a pair of diametrically opposed protrusions 110 which lie in the same plane as the remainder of washer 108. A pair of ribs 112 extend diametrically along protrusions 110 to stiffen them.

The upper surfaces of the protrusions 110 are sloped as indicated in FIG. 14, to form camming surfaces. 114. With the closure 46 in its closed position 54B, then when the button 88 and washer 108 are rotated clockwise, the protrusions 110 move underneath the bottom wall 116 bordering the recess 72, temporarily securely locking the closure 46 in closed position. If the button 88 and washer 108 are rotated a full 90 degrees from their opened unlocked position, the camming surfaces 114 of the protrusions 110 ride over wedged shaped camming projections 120 (FIG. 14) extending from the bottom wall 116 of the recess 90, so that the projections 110 then snap into a recess formed between camming projections 120 and stops 122 spaced circumferentially from projections 120. (The space between projections 120 and stops 122 is slightly greater than the width of projections 110.) It is now impossible to rotate the button and washer counterclockwise using ridge 92 at the top of the closure 46, so the closure 46 is now permanently locked in its closed position, and cannot be reopened without destruction of the closure.

The sealed container 10 can then be removed and autoclaved for sterilization of its contents, after which the container and its contents can be destroyed or otherwise dealt with in conventional fashion.

Figure 17:
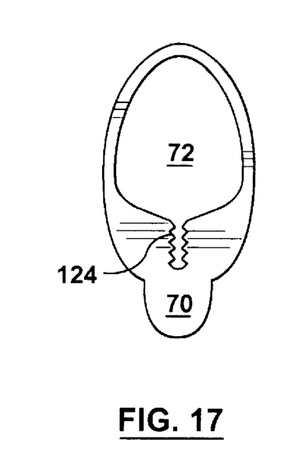
FIG. 17 is a top view of an alternative opening design for the FIG. 1 lid.

If desired, and as shown in FIG. 17, the shape of the opening 72 can be changed to provide a serrated portion 124. The serrated portion 124 can be used to grip a syringe-needle while the physician or nurse is holding the syringe barrel, thus allowing the barrel to be unscrewed from the needle, after which the needle will fall into the container.

It will be appreciated that other changes may be made in the container body and lid as described, and such changes and modifications are intended to be included within the scope of the present invention.

We claim:

1. A lid for a medical waste container, said lid comprising:
   (a) a closure hinged to said lid and movable between a first closed position and a second open position;
   (b) first and second recesses in said lid for receiving said closure when said closure is in its first and second positions respectively;
   (c) said first recess being closed and serving only to house said closure when said lid is to be open for depositing said waste;
   (d) said second recess having an opening therein to allow waste to be deposited therethrough into said container;
   (e) said closure and said second recess including at least one cooperative locking mechanism for retaining said closure in said second recess, to close said opening in said second recess.

2. A lid according to claim 1 wherein said one locking mechanism is structured to provide temporary locking of said closure in said second recess.

3. A lid according to claim 2 wherein said closure includes a finger tab projecting therefrom and adapted to be lifted by a finger to open said closure from its second position when said one locking mechanism is engaged.

4. A lid according to claim 3 wherein said locking mechanism comprises a pair of snap-fit members.

5. A lid according to claim 2 and including a second locking mechanism for providing permanent locking of said closure in said second position.

6. A lid according to claim 5 wherein said closure includes a finger tab projecting therefrom and adapted to be lifted by a finger so that said closure can be moved from said second position to said first position when said second locking mechanism is not engaged.

7. A lid according to claim 6 wherein said second locking mechanism comprises a first rotating member mounted on said closure and having a pair of protrusions extending therefrom, and said lid having a lower peripheral surface bordering said opening, said protrusions being adapted to engage beneath said lower peripheral surface for locking said closure in said second position.

8. A lid according to claim 7 and including a pair of projections extending from said lower peripheral surface, said projections being adapted to engage said protrusions for permanent locking of said closure in said second position.

9. A lid according to claim 8 wherein said closure includes a recess in its upper surface, and a second rotating member located in said recess, said second rotating member being fixedly connected to said first rotating member.

10. A lid according to claim 9 wherein said recess in said closure includes an upper surface, said second rotating member includes a handle projecting beyond said second rotating member, and said upper surface of said recess in said closure includes a pair of stops engagable with said handle to limit rotation of said second rotating member.

11. A lid according to claim 1 and including an upper surface, said closure including a flexible strap projecting therefrom and having an end remote from said closure, said end being hingedly connected to said upper surface.

12. A lid according to claim 1 and formed from polypropylene.

13. A lid according to claim 1 and mounted on a said container.

* * * * *